United States Patent [19]

Strickler

[11] Patent Number: 4,471,146

[45] Date of Patent: Sep. 11, 1984

[54] OXYDEHYDROGENATION PROCESS

[75] Inventor: Gary R. Strickler, Stow, Mass.

[73] Assignee: The Dow Chemical Company, Midland, Mich.

[21] Appl. No.: 463,436

[22] Filed: Feb. 3, 1983

[51] Int. Cl.$^3$ .......................... C07C 4/02; C07C 1/253
[52] U.S. Cl. .................................... 585/443; 585/436; 585/444
[58] Field of Search ........................ 585/436, 443, 444

[56] References Cited

U.S. PATENT DOCUMENTS

| | | | |
|---|---|---|---|
| 2,945,900 | 7/1960 | Alexander et al. | 585/443 |
| 3,298,966 | 1/1967 | Bagnetto | 585/407 |
| 3,304,342 | 2/1967 | Nolan et al. | |
| 3,315,006 | 4/1967 | Alexander et al. | 585/444 |
| 3,336,408 | 8/1967 | Capp et al. | |
| 3,392,205 | 7/1968 | Platz et al. | |
| 3,399,246 | 8/1968 | Traynor | |
| 3,595,808 | 7/1971 | Bertsch et al. | 585/629 |
| 3,607,966 | 9/1971 | Croce et al. | |
| 3,640,901 | 2/1972 | Walker | 252/437 |
| 3,641,180 | 2/1972 | Stowe et al. | 585/443 |
| 3,651,160 | 3/1972 | Reuss et al. | |
| 3,671,606 | 6/1972 | Manning | |
| 3,679,601 | 7/1972 | Nolan et al. | 252/437 |
| 3,725,493 | 4/1973 | Stine | |
| 3,743,683 | 7/1973 | Croce et al. | |
| 3,775,508 | 11/1973 | Pitzer | |
| 3,778,488 | 11/1973 | Croce et al. | |
| 3,789,078 | 1/1974 | Nolan et al. | |
| 3,801,671 | 4/1974 | Marsheck | |
| 3,856,881 | 12/1974 | Manning | |
| 3,917,732 | 11/1975 | Vrieland et al. | 585/443 |
| 3,957,897 | 5/1976 | Vrieland et al. | |
| 4,291,183 | 9/1981 | Crum et al. | 585/443 |
| 4,291,184 | 9/1981 | Crum et al. | 585/444 |

OTHER PUBLICATIONS

Carberry, J., *Chemical and Catalytic Reaction Engineering*, McGraw Hill Book Company, pp. 576–577 (1976).
Levenspiel, O., *Chemical Reaction Engineering*, Wiley & Sons, pp. 506–523 (1972).

*Primary Examiner*—Curtis R. Davis
*Attorney, Agent, or Firm*—Paul D. Hayhurst

[57] ABSTRACT

Prepare vinyl aromatic compounds in a fluidized bed by oxydehydrogenation in the presence of an alkaline earth metal-nickel phosphate catalyst.

16 Claims, No Drawings

OXYDEHYDROGENATION PROCESS

BACKGROUND OF THE INVENTION

This invention relates to a method for the preparation of alkenyl aromatic compounds. More specifically, it relates to a catalytic process for the oxydehydrogenation of alkyl aromatic compounds. Alkenyl aromatic compounds are useful as monomers and chemical intermediates. Alkenyl aromatic compounds have been prepared in the past using a number of different methods. These methods include, among others, dehydrogenation and oxydehydrogenation. See U.S. Pat. No. 4,291,183 for a brief summary of some of the known methods for preparing alkenyl aromatic compounds.

A particularly useful method for the oxydehydrogenation of alkyl aromatic compounds employs the alkaline earth-nickel phosphates disclosed in U.S. Pat. No. 3,935,126. The method disclosed in U.S. Pat. No. 3,935,126 achieves acceptable results, but is a method which leaves room for improvement.

SUMMARY OF THE INVENTION

In one aspect, the present invention is a new method for the oxydehydrogenation of alkyl aromatic compounds to alkenyl aromatic compounds. The latter compounds are prepared by contacting an alkyl aromatic compound with oxygen in a fluidized bed in the presence of an alkaline earth metal-nickel phosphate catalyst under conditions such that an alkenyl aromatic compound is formed. In another aspect, the present invention is a fluidizable bed of an alkaline earth metal-nickel phosphate catalyst.

Surprisingly, the method of the present invention enables the improved production of alkenyl aromatic compounds. The improvement may be in conversion, selectivity, yield, reduced temperature of operation, or in any combination of these. Alkenyl aromatic compounds are important starting materials for the production of resins, plastics, rubbers, solvents, chemical intermediates, and the like.

DETAILED DESCRIPTION OF THE INVENTION

Generally, the alkyl aromatic compounds of the present invention are aromatic compounds, including nitrogen-containing heterocyclics, having from 1 to 2 aromatic rings and at least one alkyl group having from 2 to 6 carbon atoms. Typical alkyl aromatic compounds include, for example, ethylbenzene, t-butyl ethylbenzene, ethyl naphthalene, isopropylbenzene, ethyl toluene, and diethylbenzene. Preferred alkyl aromatic compounds are ethyl naphthalene and t-butyl ethylbenzene. The alkyl aromatic compounds may bear inert substituents which would not be affected under the oxidative dehydrogenation conditions of the method of the present invention.

The alkyl aromatic compound may contain quantities of other hydrocarbons which do not adversely affect the oxydehydrogenation reaction, including compounds such as octane, benzene, toluene, pyridine and the like.

The process of the present invention may be employed for oxydehydrogenation of other hydrocarbon compounds such as $C_3$-$C_{10}$ alkenes and $C_4$-$C_{10}$ cycloalkenes.

The molar ratio of oxygen to alkyl aromatic compound can range from about 0.1 to about 10 moles of molecular oxygen per mole of alkyl aromatic compound, but a preferred range is from about 0.5 to about 3 and most preferred is a range of about 0.8 to about 1.5 moles $O_2$ per mole of alkyl aromatic compound. Care should be exercised to avoid explosive mixtures when feeding the alkyl aromatic compound and oxygen into the reactor.

The oxygen can be supplied as air, commercially pure oxygen, or air enriched with oxygen. Advantageously, a gaseous diluent is included in the oxygen component which is to be fed to the reactor. Suitable diluents include carbon dioxide, nitrogen, noble gases and steam, either individually or as mixtures. The diluent is normally employed in a quantity of from about zero to about 100 moles per mole of alkyl aromatic compound fed to the reactor. Preferably, from about zero to about 10 moles of diluent are employed per mole of alkyl aromatic compound.

The catalyst of the present invention is an alkaline earth metal-nickel phosphate. Typically, the first step in the preparation of the catalyst of the present invention is to prepare a catalyst according to the method described in U.S. Pat. No. 3,935,126 or the method described in U.S. Pat. No. 2,542,813; the teachings of said patents are incorporated herein by reference. The calcium form of said catalyst is preferred. Said catalyst is then reduced in size using known methods, such as grinding, and is classified by size to give a fluidizable powder that typically varies in size from about 80 to about 200 mesh. The catalyst particles are then added to a neutralized solution of $NH_4H_2PO_4$. In a preferred procedure, the pH of the slurry is adjusted to about 7 with an alkaline reagent such as ammonium hydroxide. The particles are allowed to remain in the slurry while stirring for a time sufficient to coat all available surfaces with ammonium dihydrogen phosphate. This impregnation step typically may be completed in a period of about 1 hour. It is particularly advantageous to subject the slurry to alternating periods of atmospheric and reduced pressure in such a manner that the internal surfaces of the particles are completely coated with ammonium dihydrogen phosphate. It has been found that the activity of the catalyst composition is enhanced if the catalyst particles are calcined in an inert atmosphere, such as an atmosphere of nitrogen, at a temperature between about 450° C. and about 525° C. for a period of about 2 to 4 hours.

The temperature range for conducting the reaction of the present invention may vary from about 350° C. to about 550° C. Preferably, the reaction is conducted between about 370° C. and about 500° C., most preferably between about 400° C. and about 475° C. Higher temperatures lead to rapid coking of the catalyst. Lower temperatures are undesirable due to reduced conversion which is a result of lower catalyst productivity. The reaction is typically carried out at a pressure of from about 0.1 to about 100 psig. Preferably, and for the sake of convenience, the reaction is carried out at atmospheric pressure.

The flow of materials through the reactor may vary widely, but must be sufficient to allow the reaction to proceed, and is governed by practical considerations such as convenience, reactor size and reaction temperature. Typically, the weight hourly space velocity, expressed in mass of organic compound per mass of catalyst per hour, ranges from about 0.01 to about 10. Preferably, the weight hourly space velocity is from about 0.1 to about 1. The gas hourly space velocity, expressed in volume units of gaseous feed per volume unit of catalyst bed per hour, typically ranges from about 3,000 to about 30,000. Preferably, the gas hourly space velocity is from about 6,000 to about 18,000. The gas hourly space velocity is measured at STP.

The reaction is conducted in a fluidized bed reactor which contains a fluidizable bed of at least one alkaline earth metal-nickel phosphate catalyst. Preferably, the bed includes a catalyst consisting essentially of an alkaline earth metal-nickel phosphate containing at least about 61 percent phosphate, most preferably containing from about 61 to about 70 percent phosphorus. The fluidizable bed may include inert solids. The individual particles of the fluidizable bed may be of any fluidizable particle size, although the particles typically range in size from about 30 to about 500 microns. For example, oxygen and a liquid alkyl aromatic compound are introduced into a preheater wherein the liquid is vaporized and superheated to form a gaseous mixture. Then, the gaseous mixture is forced through a coarse glass frit, typically in such a manner that very small gaseous bubbles are produced in the fluidized bed of catalyst. The floating catalyst particles mix freely with the gaseous mixture and the reaction is catalyzed. Any fluidized bed reactor in which the oxydehydrogenation reaction occurs may be employed in the process of the present invention.

When an alkyl aromatic compound is contacted with oxygen in the presence of an alkaline earth metal-nickel phosphate catalyst under the conditions hereinbefore described, an alkenyl aromatic compound is produced. The alkenyl aromatic compounds of the present invention correspond structurally to the alkyl aromatic starting materials. For example, if the alkyl aromatic compound is ethylbenzene, then the alkenyl aromatic compound is styrene. The preferred alkenyl aromatic compounds of the present invention are vinyl naphthalene, and t-butyl styrene. Preferably, the selectivity to 2-vinyl naphthalene is at least 85 mole percent when ethyl naphthalene is the alkyl aromatic compound.

The following examples are intended to illustrate the invention and should not be construed as limiting its scope. All parts and percentages are by weight unless otherwise indicated.

Preparation of Catalyst

Pellets of a commercial grade of calcium-nickel phosphate having therein organic materials, but no chromates, are crushed and calcined in air at 650° C. for approximately 9 hours in order to remove the organic materials. An aqueous 2.2 molar solution of NH$_4$H$_2$PO$_4$ neutralized with ammonium hydroxide is added to a vessel containing 5–12 mesh particles of the calcium-nickel phosphate. The particles are removed from the vessel after 15 minutes of submersion in the solution, partially dried at room temperature, and then dried at 110° C. for 16 hours. The particles are then calcined in flowing air at gradually increasing temperatures up to 550° C. The resulting particles are ground and are placed on a set of sieves capable of isolating particles ranging in size from 80 to 200 mesh. The isolated material is taken from the set of sieves and is placed in a 400-ml glass beaker. Then, 100 ml of a 2.2 molar solution of NH$_4$H$_2$PO$_4$ is prepared and is neutralized to pH 7 using ammonium hydroxide. The neutralized solution is then added to the beaker which contains the collected material. The contents of the beaker are then stirred for approximately one hour. The slurry is then filtered and the solids are placed in an oven having a temperature of 110° C. for a period of approximately 16 hours to dry.

The solids are then calcined in the presence of air for approximately 2 hours at 200° C., then for approximately 2 hours at 350° C., then for approximately 4 hours at 450° C. The calcined solids are then placed on a set of sieves which is capable of trapping particles having a size of 80–100 mesh, and the trapped solids are retained for use as a fluidizable catalyst.

EXAMPLE 1

A vertically oriented, one-piece, quartz glass, reaction vessel is used which has the following characteristics:
(a) a preheating zone comprising a quartz glass coiled tube, said tube having an outside diameter of 5.0 mm;
(b) an inlet zone comprising a 1-inch length of a quartz glass cylinder having an inside diameter of 18 mm, said inlet having at its top a quartz glass filtering frit which allows the passage of vapors but not solids;
(c) a reaction zone comprising a 2-inch length of the cylindrical material of (b); and
(d) a solid-vapor phase separation zone comprising a 3-inch long × 30 mm inside diameter cylinder which is tapered at both ends.

The vertically oriented reaction vessel is equipped with a condensing means, a means for recording and controlling temperature, and a means for monitoring the volume of materials which flow into the preheating zone.

Thirty-five grams of a fluidizable catalyst prepared according to the method described hereinabove under the heading "Preparation of Catalyst" is placed in the reaction zone of the reaction vessel, and the vessel is heated until the temperature stabilizes at 450° C. Air and t-butyl ethylbenzene are fed to the preheating zone of the reaction vessel at rates of 124 cc/minute (measured at Standard Temperature and Pressure) and 10.1 g/hour, respectively.

The alkyl aromatic compound is fed as a liquid using a pump which allows the liquid flow rate to be precisely metered. The liquid vaporizes in the preheating zone and is superheated. The mixture of air and vaporized alkyl aromatic compound pass through the frit, which fairly evenly distributes the flow of fluids into the reaction zone. The fluids enter the reaction zone and fluidize the catalyst particles. The flowing fluids then enter the solid-vapor phase separation zone, where the velocity of the flow slows sufficiently to allow the solids to drop back into the bed of catalyst. The fluids are then passed to the condensing means. The noncondensables are analyzed using a packed gas chromatograph column equipped with a thermal conductivity detector, and are then purged from the reactor system. The condensate is analyzed using a capillary gas chromatograph equipped with a flame ionization detector. The results of the analysis are summarized in Table I.

EXAMPLE 2

Following the procedure of Example 1, 40 g of catalyst is added to the empty reaction vessel. Air and ethylbenzene are fed to the reaction vessel at rates of 198 cc/minute and 11.1 g/hour, respectively. The results are summarized in Table I.

EXAMPLE 3

The procedure of Example 1 is used with the following exceptions; 10 g of catalyst is used, 10.6 g/hour of o-ethyltoluene is the alkyl aromatic compound, and 158 cc/minute of air is supplemented with 57 cc/minute of nitrogen gas. The results are summarized in Table I.

EXAMPLE 4

The procedure of Example 1 is used with the following exceptions; 25 g of catalyst having a particle size of 80–120 mesh is used, a mixture of 50 weight percent toluene and 50 percent 2-ethyl naphthalene is fed at a rate of 12 g/hour, and 10 cc/minute $O_2$ is supplemented with 140 cc/minute $N_2$. The results are summarized in Table I.

TABLE I

| Example Number | 1 | 2 | 3 | 4 |
|---|---|---|---|---|
| Alkenyl aromatic compound | t-butyl styrene | styrene | o-vinyl toluene | 2-vinyl naphthalene |
| % Conversion[1] | | | | |
| alkyl aromatic Mole % | 43.0 | 46.0 | 33.0 | 69.0 |
| Selectivity[2] | | | | |
| CO | 5.0 | 3.0 | 5.0 | 3.0 |
| $CO_2$ | 7.0 | 4.5 | 25.0 | 4.0 |
| Alkenyl aromatic compound | 83.0 | 89.5 | 63.0 | 93.0 |
| Isopropenyl styrene | <400 ppm | — | — | — |
| Other aromatics | 5.0 | 4.0 | 4.0 | 0 |

[1] % Conversion = (100) (moles of alkyl aromatic compound converted)/(moles of alkyl aromatic compound fed to reactor).
[2] Mole % Selectivity = (100) (moles of alkyl aromatic compound converted to a specific product compound)/(total of alkyl aromatic compound converted).

The preceding data is taken at 450° C., which is suprisingly lower than temperatures typically employed in oxydehydrogenation processes of the prior art, yet the percent conversion is similar to the conversions obtained by prior art processes. The lower temperature is advantageous economically and operationally, as the rate of coke formation will be reduced thereby promoting longer catalyst life and activity. Further, increased selectivity at 450° C. is observed compared to that of certain prior art methods at this temperature.

A major advantage of this invention is the decreased formation of isopropenyl styrene in the production of t-butyl styrene. Isopropenyl styrene is a troublesome cross-linker and its presence can lead to unwanted polymerization. It is produced in excess of 2000 ppm when temperatures above about 520° C. are employed in the production of t-butyl styrene. In Example 1, the reaction temperature is 450° C. and no isopropenyl styrene is detected in the effluent stream of the reactor. This indicates that the level of isopropenyl styrene is less than 400 ppm, which is the limit of the detection of the analytical equipment of Example 1.

As previously mentioned, the preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. An oxydehydrogenation process comprising contacting an alkyl aromatic compound with oxygen in a fluidized bed in the presence of an alkaline earth metal-nickel phosphate catalyst under such reaction conditions that an alkenyl aromatic compound is formed.

2. The process of claim 1 wherein the alkaline earth metal is calcium.

3. The process of claim 1 wherein the alkyl aromatic has from 1 to 2 rings, and has at least one alkyl moiety having from 2 to 6 carbons.

4. The process of claim 3 wherein the alkenyl aromatic compound is vinyl naphthalene.

5. The process of claim 3 wherein the alkenyl aromatic compound is t-butyl styrene.

6. The process of claim 3 wherein the alkenyl aromatic compound is styrene.

7. The process of claim 3 wherein the temperature is from about 350° C. to about 550° C.

8. An oxydehydrogenation process comprising contacting 2-ethyl naphthalene with oxygen in a fluidized bed in the presence of an alkaline earth metal-nickel phosphate catalyst under such reaction conditions that 2-vinyl naphthalene is formed.

9. The process of claim 8 wherein the alkaline earth metal is calcium.

10. The process of claim 9 wherein the temperature is from about 350° C. to about 550° C.

11. The process of claim 10 wherein the oxygen includes a gaseous inert diluent.

12. The process of claim 10 wherein the selectivity to 2-vinyl naphthalene is at least 85 mole percent.

13. An oxydehydrogenation process comprising contacting t-butyl ethylbenzene with oxygen in a fluidized bed in the presence of an alkaline earth metal-nickel phosphate catalyst under such reaction conditions that t-butyl styrene is formed.

14. The process of claim 13 wherein the alkaline earth metal is calcium.

15. The process of claim 14 wherein the temperature is from about 350° C. to about 550° C.

16. The process of claim 15 wherein the t-butyl ethylbenzene is para-t-butyl ethylbenzene.

* * * * *

UNITED STATES PATENT AND TRADEMARK OFFICE
CERTIFICATE OF CORRECTION

PATENT NO. : 4,471,146

DATED : September 11, 1984

INVENTOR(S) : Gary R. Strickler

It is certified that error appears in the above—identified patent and that said Letters Patent is hereby corrected as shown below:

Column 3, line 13, "phosphorus" should read

-- phosphate --.

Column 5, lines 37,38 "su-prisingly" should read

-- sur-prisingly --.

Signed and Sealed this

Second Day of April 1985

[SEAL]

Attest:

DONALD J. QUIGG

Attesting Officer   Acting Commissioner of Patents and Trademarks